(12) United States Patent
Nakao

(10) Patent No.: US 7,762,949 B2
(45) Date of Patent: Jul. 27, 2010

(54) ENDOSCOPE WITH OPEN CHANNELS

(75) Inventor: Naomi L. Nakao, New York, NY (US)

(73) Assignee: Granit Medical Innovation, LLC, New York, NY (US)

( * ) Notice: Subject to any disclaimer, the term of this patent is extended or adjusted under 35 U.S.C. 154(b) by 759 days.

(21) Appl. No.: 10/687,177

(22) Filed: Oct. 16, 2003

(65) Prior Publication Data

US 2005/0085694 A1   Apr. 21, 2005

(51) Int. Cl.
*A61B 1/00* (2006.01)

(52) U.S. Cl. ............... 600/153; 600/104; 600/111; 600/120; 600/121; 600/122; 600/123; 600/124; 600/125; 600/154; 600/155; 600/156

(58) Field of Classification Search ......... 600/121–125, 600/153, 156, 104
See application file for complete search history.

(56) References Cited

U.S. PATENT DOCUMENTS

| 2,548,602 | A | | 4/1951 | Greenburg |
| 3,495,306 | A | | 2/1970 | Eichberg |
| 3,517,702 | A | | 6/1970 | Mueller et al. |
| 3,654,049 | A | | 4/1972 | Ausnit |
| 4,646,722 | A | * | 3/1987 | Silverstein et al. ......... 600/104 |
| 4,815,470 | A | | 3/1989 | Curtis et al. |
| 4,858,286 | A | | 8/1989 | Siegel |
| 4,886,049 | A | | 12/1989 | Darras |
| 4,898,492 | A | | 2/1990 | Janowski |
| 5,025,778 | A | | 6/1991 | Silverstein et al. |
| RE34,110 | E | * | 10/1992 | Opie et al. ................... 600/128 |
| 5,154,164 | A | * | 10/1992 | Chikama .................... 600/124 |
| 5,217,001 | A | | 6/1993 | Nakao et al. |
| 5,257,617 | A | * | 11/1993 | Takahashi ................... 600/123 |
| 5,337,731 | A | | 8/1994 | Takahashi et al. |
| 5,363,838 | A | * | 11/1994 | George ....................... 600/120 |
| 5,489,256 | A | * | 2/1996 | Adair ......................... 600/133 |
| 5,503,616 | A | | 4/1996 | Jones |
| 5,643,175 | A | * | 7/1997 | Adair ......................... 600/133 |
| 5,817,015 | A | * | 10/1998 | Adair ......................... 600/121 |
| 5,840,013 | A | * | 11/1998 | Lee et al. .................... 600/114 |
| 5,938,586 | A | * | 8/1999 | Wilk et al. ................... 600/123 |
| 5,944,654 | A | * | 8/1999 | Crawford .................... 600/157 |
| 6,428,473 | B1 | * | 8/2002 | Leonard et al. ............. 600/219 |
| 6,447,445 | B1 | * | 9/2002 | Hirano ....................... 600/129 |
| 6,585,642 | B2 | * | 7/2003 | Christopher ................ 600/156 |
| 6,616,603 | B1 | * | 9/2003 | Fontana ..................... 600/199 |
| 6,929,601 | B2 | * | 8/2005 | Nakao ........................ 600/121 |
| 6,955,645 | B1 | * | 10/2005 | Zeitels ........................ 600/187 |

* cited by examiner

*Primary Examiner*—Matthew J Kasztejna
(74) *Attorney, Agent, or Firm*—R. Neil Sudol; Henry D. Coleman; William J. Sapone

(57) ABSTRACT

An endoscope with a flexible elongate insertion shaft, an illumination guide extending longitudinally through the insertion shaft, and an image guide extending longitudinally through the insertion shaft. The insertion shaft is formed along an outer surface with at least one longitudinally extending channel longitudinally traversable by an elongate endoscopic instrument. The channel having a longitudinally extending slot so that the channel is open to the ambient environment along at least a portion of its length.

13 Claims, 7 Drawing Sheets

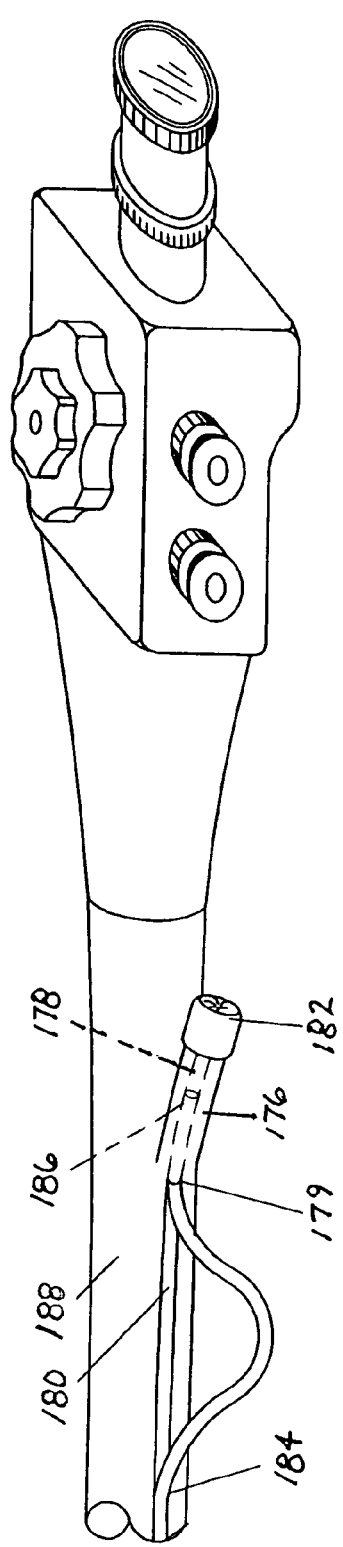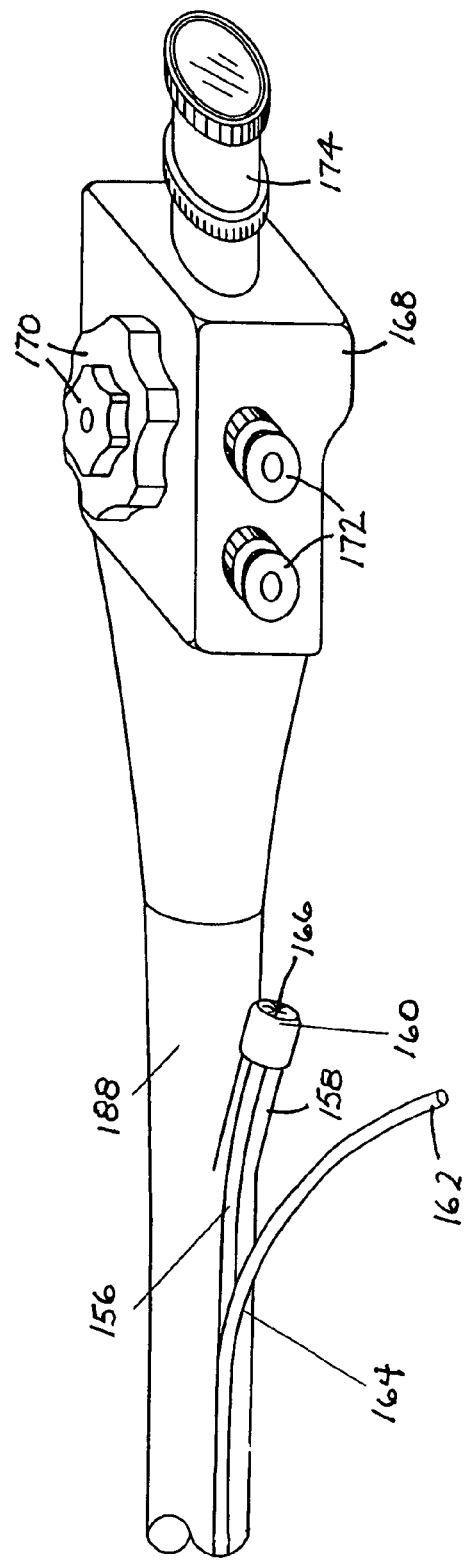
FIG. 11
FIG. 10

ENDOSCOPE WITH OPEN CHANNELS

BACKGROUND OF THE INVENTION

This invention related to endoscopes. More particularly, this invention relates to flexible fiberoptic endoscopes, i.e., endoscopes with flexible insertion members.

The flexible fiberoptic endoscope is considered according to the Food and Drug Association (FDA) and Centers for Disease Control and Prevention (CDC) to have the status of a semi-critical requirement for disinfection or sterilization. The definition of semi-critical is: "A device that comes into contact with intact mucous membranes and does not ordinarily penetrate sterile tissue". These devices should receive at least high level disinfection, defined as the destruction of all vegetative microorganisms, mycobacteria, small or non-lipid viruses, medium or lipid viruses, fungal spores and bacterial spores. The steps to achieve such disinfection are long and arduous, and all healthcare personnel in the endoscopy suite must adhere to the standard infection control recommendations in order to protect both patients and healthcare workers.

Multi-society guidelines for reprocessing flexible gastrointestinal endoscopes were presented in a position paper and delineated the following steps that must be followed during disinfection. These steps include pressure/leak testing after each use, disconnecting all air and water suction valves, meticulously cleaning channels, the outside of the entire endoscope, and all valves and connectors with an enzymatic detergent. This is followed by flushing and brushing all accessible channels to remove all organic (e.g., blood, tissue) and other residues. All surfaces must be accessed. Brushes appropriate for the channels must be used, and bristles must contact all internal surf acres of the channels. Ultrasonic cleaning of the endoscopes is used to remove soil and organic material from hard-to-clean channels inaccessible to brushes. The FDA requires disinfection with 2% gluteraldehyde for 20 minutes at 20 degrees C. The endoscope must be completely immersed in the high level disinfectant/sterilant to ensure that all channels are perfused. An automated endoscope washer-disinfector is used to ensure that all channels are adequately disinfected. Before this process is initiated, channel connectors are attached to ensure exposure of all internal surfaces with the high level disinfectant/sterilant. If this process is interrupted, disinfection process must be initiated from the beginning. "Because of design flaws of the endoscope, the staff must routinely test for infectious organisms that may be left in the channels". After high level disinfection, the channels must be rinsed with sterile, filtered or tap water to remove the disinfectant/sterilant. This is followed by flushing the channels with 70% to 90% ethyl alcohol and drying the channels with forced air. The disinfectant/sterilant is highly irritating to the colon if left inside the channels. A clinical picture similar to acute peritonitis may ensue if the colon is exposed to this noxious chemical. Personnel must use protective equipment such as gowns, eyewear, and respiratory protection devices to protect workers from exposure to the noxious chemicals. (Gastrointestinal Endoscopy, Volume 58 Number 1, July 2003 page 1).

This arduous process is necessary to avoid infection primarily because of the convoluted long and narrow channels of the endoscopes. Most infections have occurred because bioburden was not completely removed from the channels. Sterilization is rendered useless if manual cleaning is not performed perfectly.

OBJECTS OF THE INVENTION

An object of the present invention is to provide an improved endoscope, particularly a flexible fiberoptic endoscope.

It is another object of the present invention to provide an endoscope that is easier to clean and maintain than conventional endoscopes.

These and other objects of the present invention will be apparent from the drawings and descriptions herein. While it is believed that each object of the invention is attained in at least one embodiment of the invention, there is not necessarily any one embodiment that achieves all of the objects of the invention.

SUMMARY OF THE INVENTION

The invention contemplates a flexible endoscope that is easier to clean and maintain by having the working channels and suction/irrigation channel positioned on the outer wall of an endoscope and having said channels with at least a portion being open along the length of the scope's flexible insertion member.

An endoscope in accordance with the present invention comprises a flexible elongate insertion shaft, an illumination guide extending longitudinally through the insertion shaft, and an image guide extending longitudinally through the insertion shaft, the insertion shaft being formed along an outer surface with at least one longitudinally extending channel longitudinally traversable by an elongate endoscopic instrument, the channel having a longitudinally extending slot.

Pursuant to a feature of the present invention, the endoscope further comprises a closure member removably connected to the insertion shaft to close the slot. Where the channel has a distal end opening and proximal end opening, the slot extending from the distal end opening to the proximal end opening, the closure member closes the slot while maintaining the distal end opening and the proximal end opening unobstructed. The closure member may take the form of an endoscope sheath circumferentially surrounding the insertion shaft. Alternatively, where the insertion shaft is formed with a pair of opposing edges along the slot, the closure member may take the form of an elongate strip removably attached to the insertion shaft at the edges. In the latter case, at least one of the closure member and the insertion shaft may be provided with a groove, while the other is inserted into the groove to removably attach the closure member to the insertion shaft.

Pursuant to another feature of the present invention, the endoscope may include a catheter removably disposed in the channel to serve as a channel liner. The catheter may be held in the channel by a snap-lock fit, where the catheter is made of a resilient material and has a diameter larger than the width of the slot in the channel. Alternatively or additionally, where a closure member such as a sheath is provided, the closure member may hold the catheter in the channel. In the case of a sheath, the catheter may be fastened to the sheath.

The catheter and the closure member each assist in the passing of endoscopic accessories along the channel or allow for the application of suction and/or irrigation along the endoscope insertion shaft.

The sheath is preferably an elongate strip wound about the insertion shaft and provided with an adhesive closure. More specifically, the sheath may take the form of an elongate web member or strip disposable in a tubular configuration in engagement with the endoscope insertion member and provided with a tensile member serving as a tear string. The tear string preferably extends longitudinally along the web member. In addition, the tear string preferably extends from one end of the web member to an opposite end thereof.

The sheath is provided in a plurality of regions with a layer of adhesive material. The adhesive material of at least one of the regions is permanent adhesive, whereas the adhesive material of at least another of the regions forms a separable bond. These regions extend along opposing longitudinal edges of the web member, at least where web member is a rectangular sheet.

The sheath may be provided with an end cap securable over a distal tip of the endoscope insertion member in a fluid tight engagement with the web member. The end cap is secured or securable to an end of the web member. The end cap is provided with an opening alignable with the external channel on the endoscope insertion member.

The catheter may be provided at a proximal end with connectors for coupling the catheter to a source of irrigation fluid and a source of suction.

Pursuant to additional features of the present invention, the channel extends from a proximal end portion of the insertion shaft to a distal tip thereof, has a mostly circular cross-section divided by the slot, and is defined by a surface of the insertion member having a C-shaped cross-section.

In one embodiment of the invention, the channel is a one of a pair of channels formed along the outer surface of the insertion shaft, the channels being circumferentially spaced from one another. The channels may, for example, be disposed along diametrically opposed sides of the insertion member.

In another embodiment of the invention, the channel has a pair of lobes, each defined by a surface of the insertion member having a C-shaped cross-section. A catheter insertable into this dual-lobe channel has a cross-section substantially in the form of a FIG. 8.

An endoscope in accordance with the present invention may be packaged as an endoscope assembly comprising (a) an elongate flexible endoscope insertion member provided with at least one channel along an outer cylindrical surface, the channel being open along the surface, and (b) an elongate closure member removably attachable to the insertion member so as to close the channel along the cylindrical surface. As discussed above, the closure member may take the form of a sheath windable about the insertion member or, alternatively, an elongate strip removably attached to the insertion shaft at edges of a slot therein which communicates with the channel. The assembly may also comprise a catheter removably disposable in the channel.

An endoscope in accordance with the present invention has a flexible insertion member provided with an external or outer layer of biocompatible elastomeric material that is sufficiently rigid to substantially maintain its shape yet enough flexibility to accommodate the range of expected endoscope use configurations. The channels may be of more than one size, limited essentially by the size of the endoscope. The channels may be utilized for a variety of medical activities including, but not limited to, irrigation, suction, biopsy, injection, and tissue and foreign body extraction.

The present invention greatly facilitates endoscope cleaning and sterilization owing to the ease of access to all surface of the endoscope that may come into contact with biomaterials. The irrigation, suction and biopsy channels are all part of the continuous external surface of the endoscope insertion member and are easily cleaned. The present invention obviates the following cleaning and sterilization processes necessary to the continued use of conventional endoscopes having biopsy channel open only at the distal tip and the proximal terminus: 20 minutes of soaking, complete immersion of the scope in a cleaning liquid, special brushing, forced delivery of cleaning fluid, forced delivery of rinsing solution, ultrasonic cleaning, and air pressure drying.

BRIEF DESCRIPTION OF THE DRAWINGS

FIG. 10 is a perspective view of a proximal end of an endoscope in accordance with the present invention.

FIG. 11 is a perspective view of a proximal end of another endoscope in accordance with the present invention.

DETAILED DESCRIPTION

Figure 1:
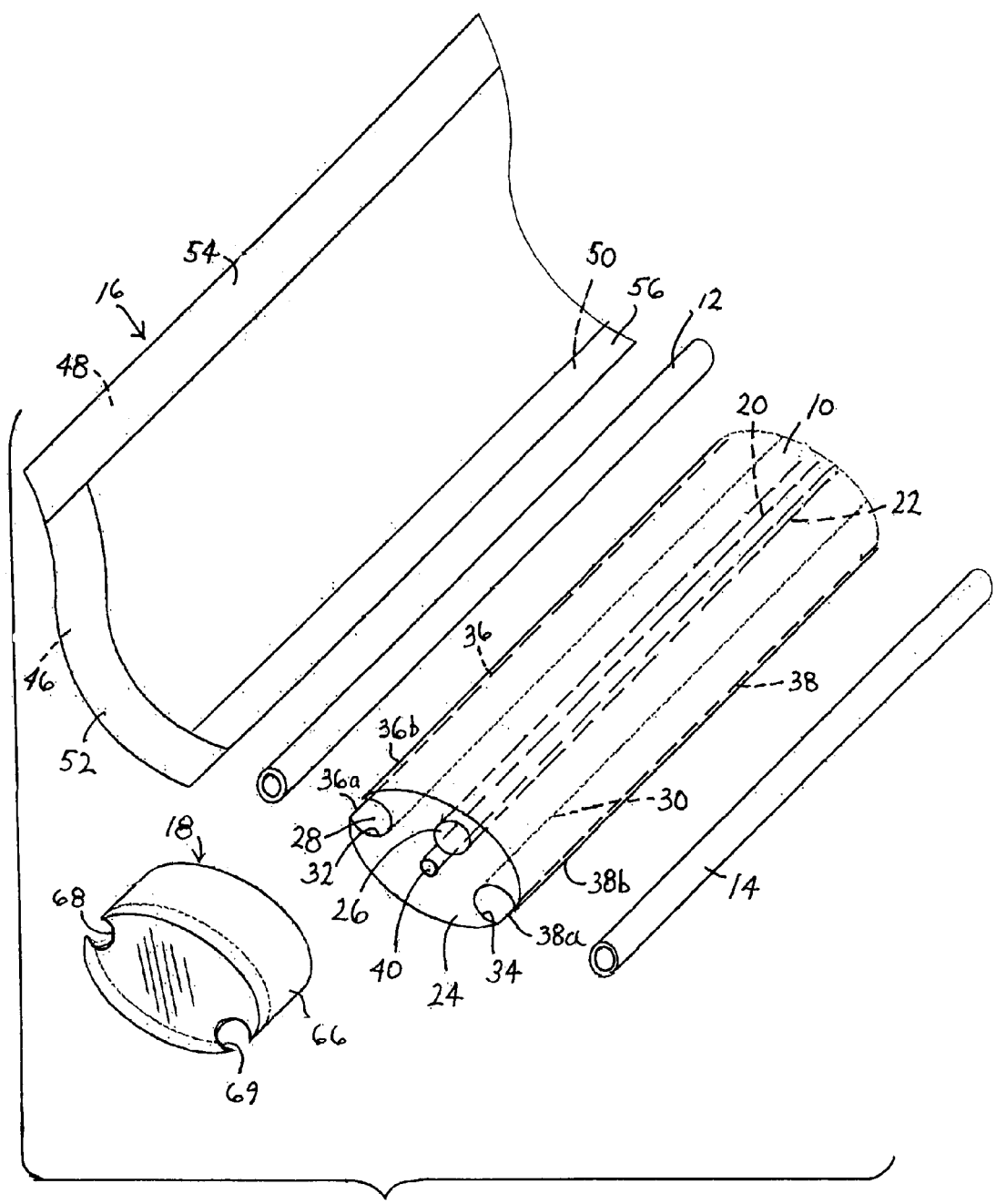
FIG. 1 is an exploded schematic perspective view of an endoscope assembly or kit in accordance with the present invention.
Figure 2:
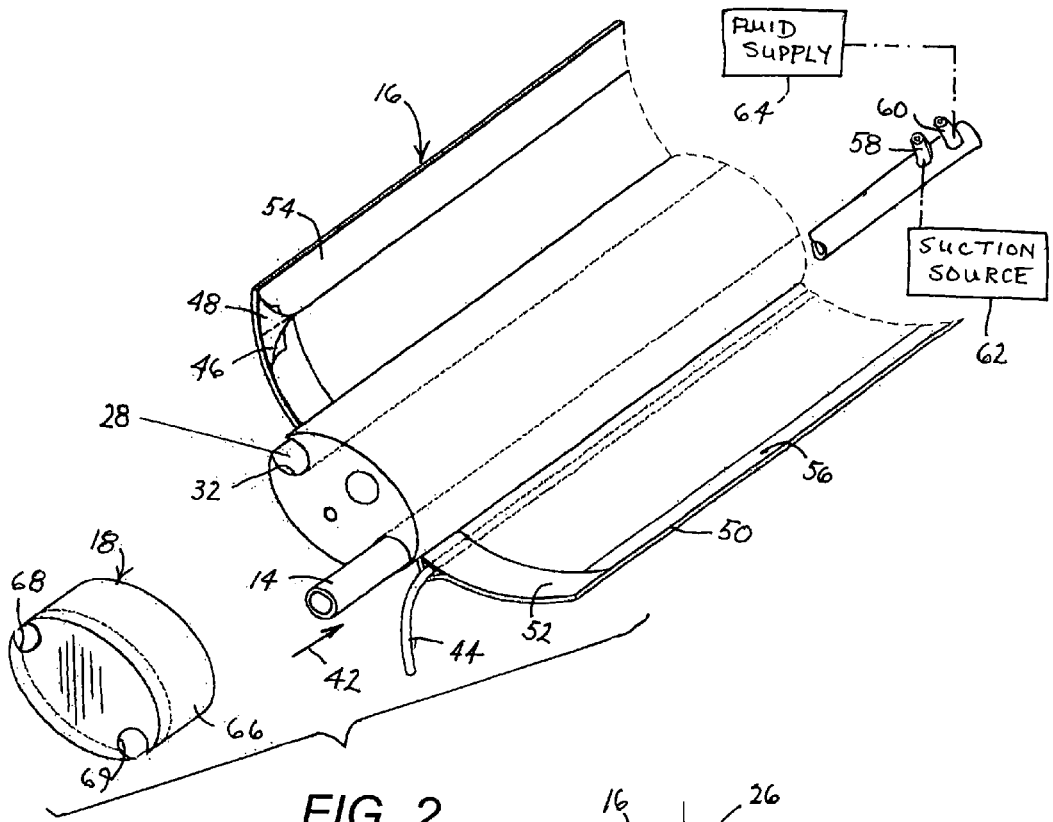
FIG. 2 is a schematic perspective view of the endoscope assembly of FIG. 1 in a partially assembled configuration.

As depicted in FIGS. 1 and 2, an endoscope assembly comprises a flexible elongate insertion member or shaft 10, a pair of catheters 12 and 14, a sheath 16, and optionally an end cap 18. Insertion shaft 10 includes a longitudinally extending illumination guide 20 and a longitudinally extending image guide 22. Image guide 22 may take the form of a fiber-optic bundle or, alternatively, an electrical cable. In the latter case, a charged coupled device or other camera (not shown) is disposed at the distal end 24 of the insertion shaft 10 for converting incoming electromagnetic waves into a digitized electrical signal encoding video images. In either case, a lens 26 is provided at the distal tip of image guide 22 for focusing the incoming electromagnetic waves.

As further depicted in FIGS. 1 and 2, insertion shaft 10 is provided along an external surface (not separately designated) with a pair of C-profile channels 28 and 30 approximately opposing one another. Channels 28 and 30 communicate with the ambient environment not only via respective distal end openings 32 and 34 and proximal end openings (not shown) but also via respective longitudinal slots 36 and 38. Slots 36 and 38 are defined by opposing longitudinal edges 36a, 36b and 38a, 38b formed along the outer surface of endoscope insertion shaft 10. Channels 28 and 30 each have a transverse dimension or diameter, while the respective slots 36 and 38 each have transverse dimension or width (distance between opposing longitudinal edges 36a and 36b for slot 36 or between edges 38a, 38b for slot 38) substantially smaller than the transverse dimension or diameter of the respective channel. Opposing longitudinal edges 36a, 36b and 38a, 38b are along turned-in portions of the outer surface of endoscope insertion shaft 10, that is, opposing longitudinal edges 36a, 36b (or 38a, 38b) extend towards one another to define the C-shaped profile of the channels 28, 30.

An exit aperture 40 of illumination guide 20 forms a working light source for the endoscope. That aperture 40 and viewing lens 26 are positioned approximately at the center of the endoscope insertion shaft 10 to allow for adequate configuration of the scope control assembly so that the distal end 24 of the endoscope can be maneuvered in much the same manner as in current endoscopes.

Generally, it is preferred that catheters 12 and 14 are disposed in channels 28 and 30 during use of the endoscope assembly inside a patient. The catheters 28 and 30 have diameters that are larger than the widths of slots 36 and 38 but smaller than the diameters of channels 28 and 30. Thus, as indicated by an arrow 42 in FIG. 2, catheters 12 and 14 may be slid longitudinally into channels 28 and 30 during an assembly procedure. Alternatively, catheters 12 and 14 may be made a material that is sufficiently resilient to permit a transverse introduction of the catheters into channels 28 and 30, i.e., through slots 36 and 38.

Preferably after the disposition of catheters 12 and 14 in channels 28 and 30, sheath 16 is wound about and attached to insertion shaft 10. Sheath 16 takes the form of an elongate rectangular web member or strip disposable in a tubular configuration in engagement with endoscope insertion member 10 and provided with a tensile member 44 serving as a tear string. Tear string 44 extends longitudinally along the sheath 16 from a distal end of sheath 16 to a proximal end thereof.

Figure 3:
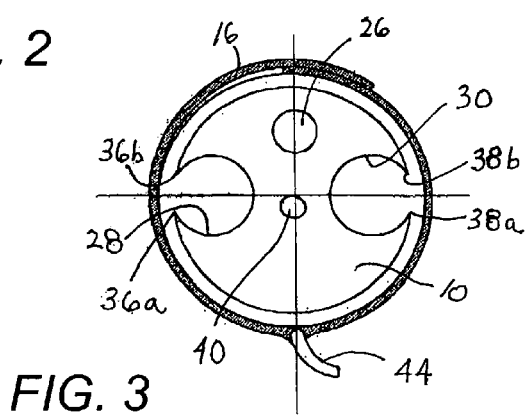
FIG. 3 is a schematic distal end elevational view of a modified endoscope assembly in accordance with the present invention.

Sheath 16 is provided along a transversely extending edge region 46 and a first longitudinal edge region 48 with a layer of releasable adhesive. The adhesive material of region 46 and 48 forms a separable bond. Sheath 16 is further provided on a second longitudinal edge region 50 with a layer of permanent adhesive material. Protective cover strips 52, 54, and 56 are removably attached to the adhesive layers of regions 46, 48, and 50 at the time of manufacture. To attach sheath 16 to insertion shaft 10, cover strips 52, 54, and 56 are removed from adhesive regions 46, 48, and 50. Endoscope insertion member 10 is then placed over the longitudinal center of sheath 16 as shown in FIG. 2. The half of the sheath 16 longitudinally bounded by adhesive region 48 is then wrapped around insertion shaft 10. Regions 46 and 48 are pressed to the outer surface of the shaft to form a temporary bond thereto. Then the other half of sheath 16, which is longitudinally bound by adhesive region 50, is wrapped around shaft 10, with region 50 being pressed against an outer surface of the sheath to form a permanent bond therewith. The assembled configuration, minus the catheters 12 and 14, is shown in FIG. 3.

Sheath 16 is preferably made of a fine film material that would be easily punctured or torn by insertion of an endoscopic surgical or diagnostic instrument. A catheter 12 or 14 that used for the insertion of endoscopic instruments thus serves to protect sheath 16 from inadvertent damage. The other catheter 14 or 12 is provided at a proximal end with connectors or couplings 58 and 60 for the operative engagement of a suction source 62 and an irrigation fluid supply 64.

Accordingly, one channel 28 or 30 serves for the passage of endoscopic accessories such as forceps, snares, needles, etc. (none shown), while the other channel 30 or 28 permits connection to suction source 62 and irrigation fluid source 64. These "C" channels 28 and 30 are substantially easier to clean and disinfect than the biopsy channel of conventional endoscopes since the channels 28 and 30 are open on the outside of the scope, allowing for easy brushing and full contact with disinfectant.

Figure 4:
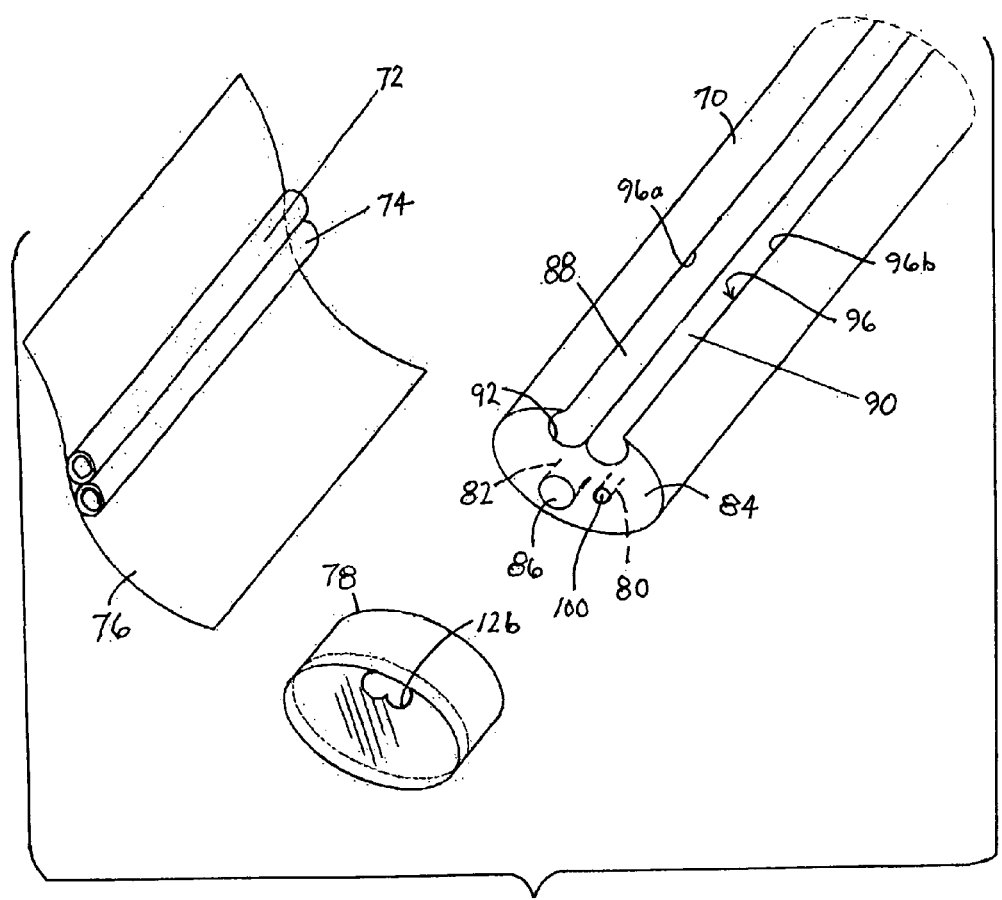
FIG. 4 is an exploded schematic perspective view of another endoscope assembly or kit in accordance with the present invention.
Figure 5:
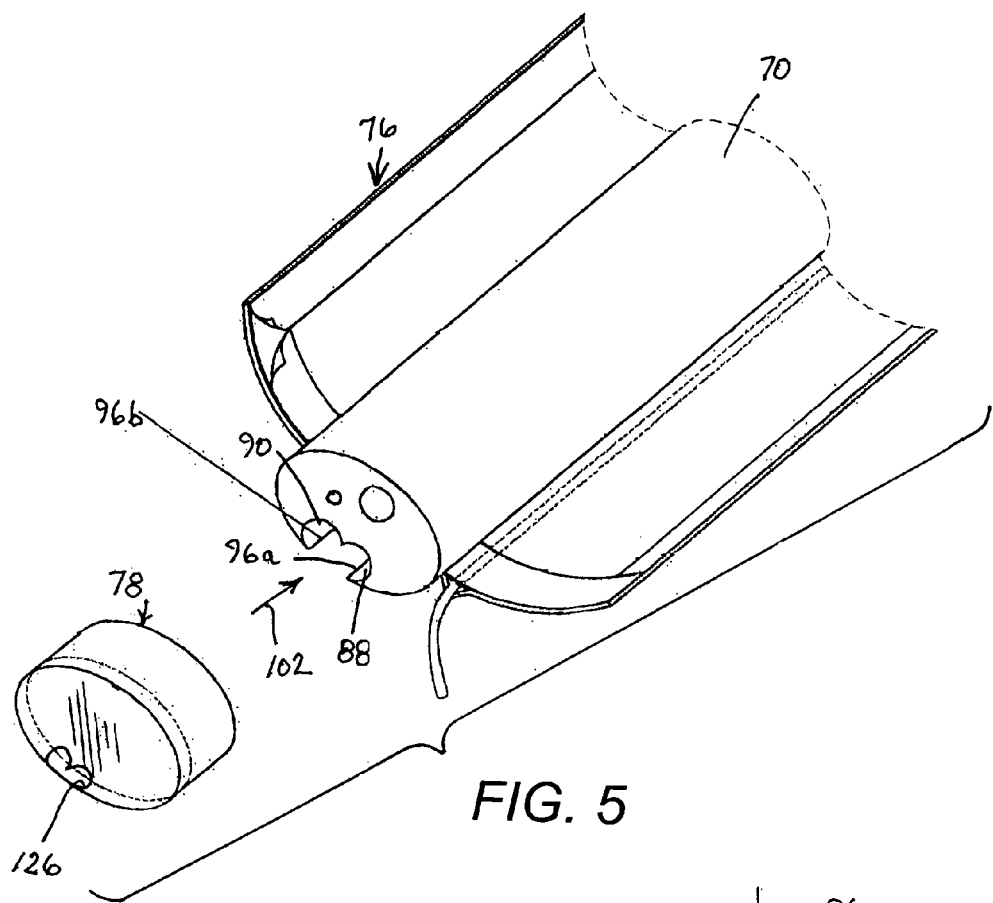
FIG. 5 is a schematic perspective view of the endoscope assembly of FIG. 4 in a partially assembled configuration.
Figure 6:
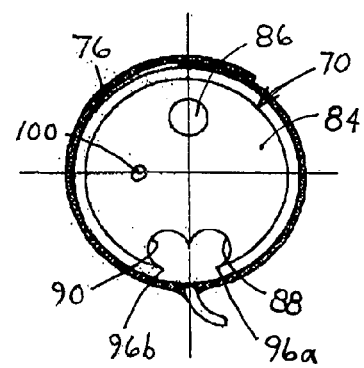
FIG. 6 is a schematic distal end elevational view of another modified endoscope assembly in accordance with the present invention.

As an optional step in the preparation of the endoscope assembly for use in a patient, end cap 18 may be placed over the distal end 24 of insertion shaft 10 prior to the placement of shaft 10 on the open sheath 16 and concomitantly prior to the wrapping of sheath 16 about shaft 10. In that case, adhesive region 46 is placed into contact with an annular flange 66 of end cap 18. In this case, adhesive region 46 may be provided with a permanent adhesive for firmly gripping the end cap. End cap 18 is provided with openings 68 and 69 alignable with channels 28 and 30, respectively As illustrated in FIGS. 4-6, another endoscope assembly comprises a flexible elongate insertion member or shaft 70, a pair of catheters 72 and 74, a sheath 76, and optionally an end cap 78. Insertion shaft 70 includes a longitudinally extending illumination guide 80 and a longitudinally extending image guide 82. Image guide 82 may take the form of a fiber-optic bundle or, alternatively, an electrical cable. In the latter case, a charged coupled device or other camera (not shown) is disposed at the distal end 84 of the insertion shaft 70 for converting incoming electromagnetic waves into a digitized electrical signal. In either case, a lens 86 is provided at the distal tip of image guide 82 for focusing the incoming electromagnetic waves.

As further depicted in FIGS. 4 and 5, insertion shaft 70 is provided along an external surface (not separately designated) with a pair of contiguous C-profile channels 88 and 90. Channels 88 and 90 communicate with the ambient environment not only via a mutual dual-lobe distal end opening 92 and one or more proximal end openings (not shown) but also via a common longitudinal slot 96. Slot 96 is defined by opposing longitudinal edges 96a, 96b formed along the outer surface of endoscope insertion shaft 70.

An exit aperture 100 of illumination guide 80 forms a working light source for the endoscope. Aperture 100 and viewing lens 86 are positioned approximately at the center of the endoscope insertion shaft 70 to allow for adequate configuration of the scope control assembly so that the distal end 84 of the endoscope can be maneuvered in much the same manner as in current endoscopes.

Generally, it is preferred that catheters 72 and 74 are disposed in channels 88 and 90 during use of the endoscope assembly inside a patient. Catheters 88 and 90 have a combined width that is larger than the width of slot 96. Catheters 88 and 90 have respective diameters that are smaller than the diameters of channels 88 and 90. Thus, as indicated by an arrow 102 in FIG. 5, catheters 72 and 74 may be slid longitudinally into channels 88 and 90 during an assembly procedure. Alternatively, catheters 72 and 74 may be made a material that is sufficiently resilient to permit a transverse introduction of the catheters into channels 88 and 90, i.e., through slot 96.

As shown in FIG. 4, catheters 72 and 74 may be pre-attached to sheath 76. In that case, catheters 72 and 74 must be inserted into channels 88 and 90 prior to a wrapping of sheath 76 about insertion shaft 70 and an adhesive attachment thereto as discussed above with reference to FIGS. 1-3. Sheath 76 is thus similar to sheath 16 except for the pre-attachment of catheters 72 and 74.

Accordingly, one channel 88 or 90 serves for the passage of endoscopic accessories such as forceps, snares, needles, etc.

(none shown), while the other channel 90 or 88 permits connection to suction source 122 and irrigation fluid source 124. These "C" channels 88 and 90 are substantially easier to clean and disinfect than the biopsy channel of conventional endoscopes since the channels 88 and 90 are open on the outside of the scope, allowing for easy brushing and full contact with disinfectant.

As an optional step in the preparation of the endoscope assembly for use in a patient, end cap 78 may be placed over the distal end 84 of insertion shaft 70. End cap 78 is provided with a dual-lobe opening 126 alignable with channels 88 and 90.

It is possible to omit both catheters 12 and 14 from the assembly of FIGS. 1-3 and similarly to omit both catheters 72 and 74 from the assembly of FIGS. 4-6. In that case, the endoscopic instruments inserted through a channel 28 or 30 and 88 or 90 preferably have blunt tips resulting in a reduced probability of damage to sheaths 16 and 76. Sheaths 16 and 76 have sufficient strength and are wound sufficiently tight to enable the transmission of fluids under negative pressure (suction) or positive pressure (irrigation) through the other channel.

In another variation of the embodiments of FIGS. 1-3 and 4-6, it is possible to use catheters 12 and 14 without sheath 16 and catheters 72 and 74 without sheath 76. Catheters 12 and 14 are held in channels 28 and 30 and catheters 72 and 74 in channels 88 and 90 by virtue of the geometry of the catheters and the channels. The diameters of the catheters and the channels may be so close that the catheters are held in the channels by a friction lock fit. In this case, catheters 72 and 74 may be connected to one another along their lengths to form a double lumen catheter. One lumen of this double lumen catheter has a connector at the proximal end for the suction and irrigation apparatus while the second lumen is used for endoscopic accessories. At the start of the procedure the sterile "FIG. 8" catheter is inserted into the "C" channel of the endoscope and secured there by either a compression fit, sheath 76 or other mechanism appropriate to the scope and clinical procedure. At the conclusion of the endoscopy the sheath, if used, would be disposed of as well as the "FIG. 8" catheter. The scope can then be easily cleaned and disinfected. In another design (not shown) the FIG. 8 catheter is inserted through one "C" channel 88 or 90 only with one of the loops of the FIG. 8. The other lumen would protrude out.

In a further variation of the embodiment of FIGS. 1-3, at least one of the channels 28 and 30 may be used in a naked condition, without a catheter 12, 14 and without sheath 16. In that case, endoscopic instruments are inserted through that channel 28 or 30 and are maintained in the channel because the respective slot 36 or 38 is too narrow to permit the escape of the instrument shaft from the channel. If irrigation or suction is necessary for the particular endoscopic procedure, the other channel 30 or 28 is provided with a respective catheter 14 or 12 for the conduction of fluids in the proximal direction in the case of suction and in the distal direction in the case of irrigation.

Figure 7:
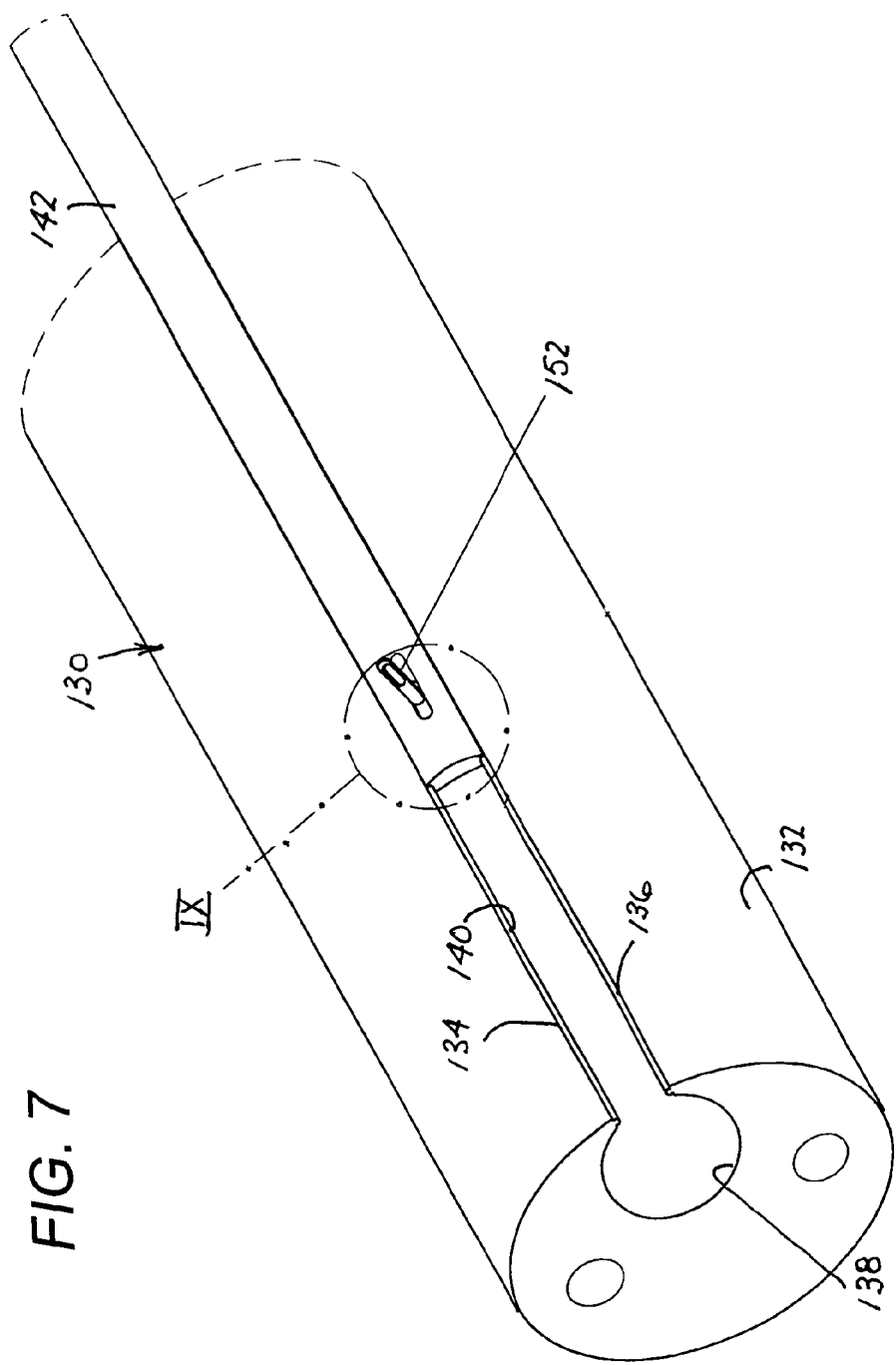
FIG. 7 is a schematic isometric view, on an enlarged scale, of an endoscope insertion member provided with an external, open biopsy channel and a slidable closure member in accordance with the present invention.
Figure 9:
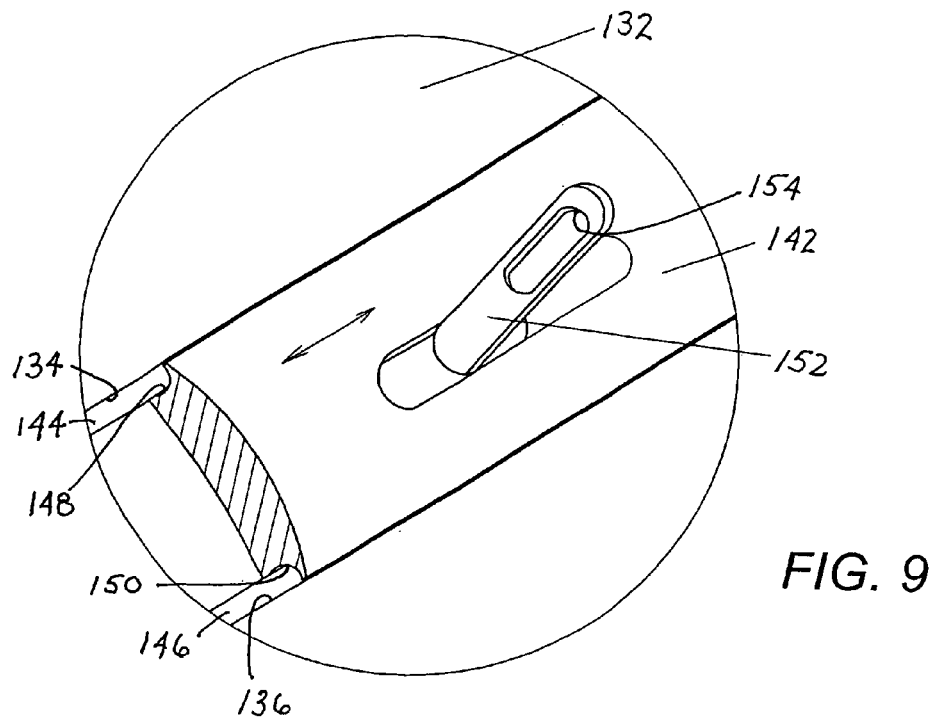
FIG. 9 is a schematic isometric view, also partially cut away and on the larger scale, of the detail encircled at IX in FIG. 7.
Figure 8:
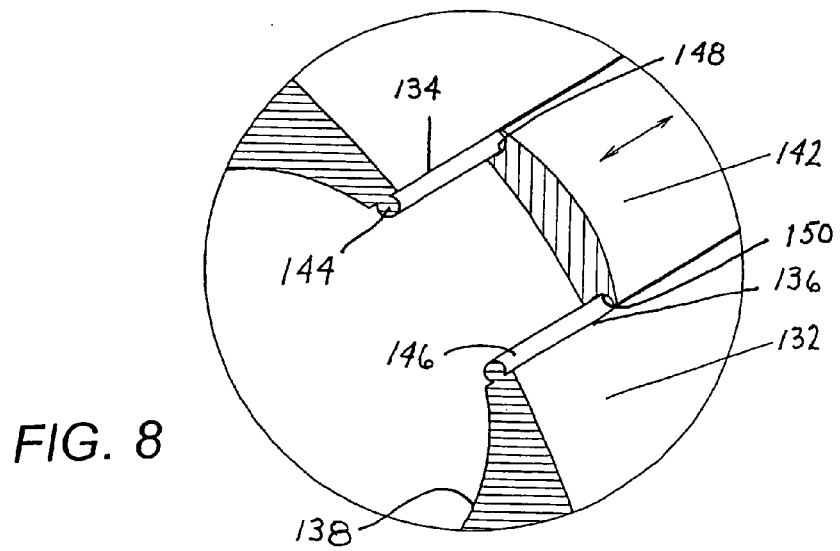
FIG. 8 is a schematic isometric view, partially cut away and on an even larger scale, of a portion of the endoscope insertion member with the channel and slidable closure of FIG. 7.

As illustrated in FIGS. 7-9, an endoscope insertion member or shaft 130 is formed along an outer surface 132 with a longitudinal channel 138 having a pair of opposing edges 134 and 136 defining a longitudinal slot 140. An elongate closure member 142 made, for instance, of a thermoplastic resin material, is slidably engaged with insertion member 130 along edges 134 and 136 to cover or close slot 140 during at least a portion of an endoscopic investigation. Channel 138 has a substantially circular cross-section, while closure member 142 is substantially disposed only outside of that circular cross-section, the closure member being configured to not protrude into the channel and to substantially maintain and complete the circumference of the circular cross-section thereof. Closure member has a pair of parallel longitudinal edges that engage respective opposing edges 134 and 136 to close slot 140.

As shown in FIG. 8, edges 134 and 136 may be formed with respective ribs 144 and 146 that are received in respective grooves 148 and 150 on closure member 142. As shown in FIG. 9, closure member 142 is provided with a pivotably mounted pull-tab 152 in turn formed with an eyelet 154. Pull-tab 152 serves as an entrainment element enabling a technician or endoscopist to pull closure member 142 along slot 140 at least during an installation operation prior to a diagnostic or therapeutic endoscopic procedure. Pull-tab 152 is preferably provided at a proximal end of closure member 142. Together with closure member 142, a tool with a hook (not shown) may be provided as part of an endoscope closure kit, where the hook is inserted through eyelet 154 for entrainment purposes. Another kind of entrainment element engageable by such a hook tool would be a simple aperture or recess in the closure member 142.

FIG. 10 depicts the proximal end of an endoscope insertion member 188 having a biopsy channel 156 open along its length as described hereinabove. Channel 156 extends in the proximal direction along insertion member 154 to a stiff biopsy channel entry port 158 that diverges outwardly from the insertion member. A tubular channel liner 164 in the form of a catheter resiliently and removably snaps into the open channel 156. At a proximal end, liner 164 extends out 1-2 cm and is covered by a rubber end cap 160 attached with a pressure fit. End cap 160 is made of a polymeric material and is provided with a valve port 166 through which a flexible endoscopic instrument (not shown) may be inserted into channel liner 164 and along the length of channel 156. A control head 168 has directional control knobs 170, irrigation and suction ports 172 and an eyepiece 174.

As depicted in FIG. 11, a channel liner 184 in the form of a catheter lays in an open biopsy channel 180 along the shaft or insertion member 154 of the endoscope until a bifurcation 179 between the shaft or insertion member and a biopsy channel entry port 176, which is not flexible. Here liner 184 enters a closed channel segment or lumen 178. Liner 184 exits from a proximal end of the biopsy channel entry port 176 and extends out for about 1-2 cm. A rubber end cap 182 then is pressure fitted to the free, extending end (not shown) of liner 184. Liner 184 resiliently and removably snaps into the open channel 180

End caps or port elements 160 and 182 are placed on the channel liners 164, 184 about 2-3 inches from the endoscope insertion member 154. Once an endoscopic procedure has been completed using the endoscope of FIG. 10 or 11, one can cut off end cap or port element 160 or 182 from the respective biopsy channel liner 164 or 184, plug up the channel liner, and then pull it out of the open biopsy channel 156, 180. This procedure facilitates the maintenance of cleanliness. Brushing, cleaning and rinsing procedures are simplified if not obviated.

Of FIGS. 10 and 11, the preferred embodiment here is FIG. 11 because entry port 176, where instruments are first inserted, is completely surrounded by solid matter. There is an angle between the entry port 176 and the endoscope shaft 154. If the channel 178 were open, the liner 184 with an endoscopic instrument inside could pop out. Moreover, the entrance way provides more protection during the critical entry of the operating instrument.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A flexible endoscope comprising a flexible elongate insertion shaft incorporating an image-carrying component and having a circumference, said insertion shaft being formed with at least one longitudinally extending substantially circular channel, said channel including a longitudinal slot contiguous with an outer surface of said insertion shaft, said slot having a transverse dimension smaller than any diameter of said channel; a closure member configured to close said channel, said closure member being an elongate strip formed with a pair of parallel longitudinal edges configured to attach to respective opposing edges of said longitudinal slot of said insertion member, at least one of said closure member and said insertion shaft being provided with a groove, the other of said closure member and said insertion shaft being insertable into said groove to removably attach said closure member to said insertion shaft, said closure member completing the circumference of said insertion member.

2. The endoscope defined in claim 1 wherein said channel has a distal end opening and proximal end opening, said slot extending from said distal end opening to said proximal end opening, said closure member closing said slot while maintaining said distal end opening and said proximal end opening unobstructed.

3. The endoscope defined in claim 1, further comprising a catheter disposed in said channel.

4. The endoscope defined in claim 3 wherein said closure member is disposed over said channel and said catheter.

5. The endoscope defined in claim 1 wherein at a proximal end said channel terminates at an entry port bifurcated with respect to and diverging from said shaft, further comprising a biopsy channel liner removably disposed in said channel and extending at a proximal end out of said entry port, an end cap being fitted to said liner at said entry port.

6. The endoscope defined in claim 5 wherein said entry port defines a closed lumen communicating with said channel.

7. The endoscope defined in claim 5 wherein said channel continues open along said entry port.

8. The endoscope defined in claim 1 wherein said channel extends from a proximal end portion of said insertion shaft to a distal tip thereof.

9. The endoscope defined in claim 1 wherein said closure member is slidably connected to said insertion shaft, said closure member being provided with an entrainment element for facilitating manipulation of said closure member to slide said closure member along said slot.

10. The endoscope defined in claim 9, wherein said entrainment member is a pull tab.

11. The endoscope defined in claim 1 wherein said outer surface of said insertion shaft is a first outer surface and said closure member has a second outer surface, said second outer surface being smoothly continuous with said first outer surface.

12. The endoscope defined in claim 11 wherein said closure member is arcuate in transverse cross-section, completing the circumference of said insertion member.

13. A flexible video endoscope comprising a flexible elongate insertion shaft incorporating a video-image-carrying component and having a circumference, said insertion shaft being formed with at least one longitudinally extending substantially circular channel, said channel including a longitudinal slot contiguous with an outer surface of said insertion shaft, said slot having a transverse dimension smaller than any diameter of said channel; a closure member configured to close said channel, said closure member being an elongate strip formed with a pair of parallel longitudinal edges configured to attach to respective opposing edges of said longitudinal slot of said insertion member, at least one of said closure member and said insertion shaft being provided with a groove, the other of said closure member and said insertion shaft being insertable into said groove to removably attach said closure member to said insertion shaft, said closure member completing the circumference of said insertion member.

* * * * *